(12) United States Patent
Schweitzer et al.

(10) Patent No.: US 11,867,681 B2
(45) Date of Patent: Jan. 9, 2024

(54) TOC ANALYZER AND METHOD FOR MOISTENING A BINDER IN A TOC ANALYZER

(71) Applicant: ENDRESS+HAUSER CONDUCTA GMBH+CO. KG, Gerlingen (DE)

(72) Inventors: Daniel Schweitzer, Remshalden (DE); Ulrich Kathe, Ludwigsburg (DE); Michael Ingelmann, Vaihingen/Enz (DE)

(73) Assignee: Endress+Hauser SE+Co. KG, Gerlingen (DE)

( * ) Notice: Subject to any disclaimer, the term of this patent is extended or adjusted under 35 U.S.C. 154(b) by 233 days.

(21) Appl. No.: 17/645,158

(22) Filed: Dec. 20, 2021

(65) Prior Publication Data

US 2022/0196627 A1    Jun. 23, 2022

(30) Foreign Application Priority Data

Dec. 21, 2020   (DE) .......................... 102020134417.1

(51) Int. Cl.
*G01N 33/18*   (2006.01)

(52) U.S. Cl.
CPC ................ *G01N 33/1846* (2013.01)

(58) Field of Classification Search
CPC ........................... G01N 18/1826; G01N 18/18
USPC .......................................... 73/61.41, 864.81
See application file for complete search history.

(56) References Cited

U.S. PATENT DOCUMENTS

| 1,515,237 | A | 11/1924 | Yensen | |
|---|---|---|---|---|
| 2011/0076198 | A1* | 3/2011 | Bettmann | .......... G01N 33/1846 422/78 |
| 2017/0321505 | A1* | 11/2017 | Murphy | .................. E21B 41/00 |

FOREIGN PATENT DOCUMENTS

| CN | 101573615 A | 11/2009 |
|---|---|---|
| CN | 101636225 A | 1/2010 |
| CN | 102047110 A | 5/2011 |
| CN | 102362180 A | 2/2012 |
| CN | 102365547 A | 2/2012 |
| CN | 102388301 A | 3/2012 |
| CN | 102428362 A | 4/2012 |
| CN | 202974980 U | 6/2013 |
| CN | 106237636 A | 12/2016 |
| CN | 111273045 A | 6/2020 |
| DE | 3909240 A1 | 9/1990 |
| DE | 102006058051 A1 | 6/2008 |

(Continued)

*Primary Examiner* — Nathaniel J Kolb
(74) *Attorney, Agent, or Firm* — Christopher R. Powers; Endress+Hauser (USA) Holding, Inc.

(57) ABSTRACT

A TOC analyzer for determining a carbon content of a sample includes: a processing unit for removing carbon dioxide gas from the carrier gas before the oxidation of the sample, wherein the processing unit has a binder for binding the carbon dioxide gas from the carrier gas, wherein a defined water content is provided within the binder, wherein the processing unit is configured for moistening the binder by means of water vapor contained in the carrier gas; a condensation unit for condensing the water vapor resulting from the vaporization and/or oxidation of the sample to form a condensate, wherein the condensation unit has an outlet for the condensate toward a moistening unit; and the moistening unit for moistening the carrier gas by means of the condensate. A method for moistening a binder using such a TOC analyzer is further disclosed.

13 Claims, 4 Drawing Sheets

(56) References Cited

FOREIGN PATENT DOCUMENTS

DE 102009001861 A1 9/2010
EP 0388589 A2 9/1990

* cited by examiner

TOC ANALYZER AND METHOD FOR MOISTENING A BINDER IN A TOC ANALYZER

CROSS-REFERENCE TO RELATED APPLICATION

The present application is related to and claims the priority benefit of German Patent Application No. 10 2020 134 417.1, filed on Dec. 21, 2020, the entire contents of which are incorporated herein by reference.

TECHNICAL FIELD

The present disclosure relates to a TOC analyzer for determining a carbon content of a sample, wherein the sample is present in water. The invention further relates to a method for moistening a binder in a TOC analyzer.

BACKGROUND

A TOC analyzer determines at least the TOC content, i.e., the "total organic carbon" content, in a sample. TOC analyzers sometimes additionally determine the TIC, i.e., the "total inorganic carbon" content, or the TC, i.e., the "total carbon" content. The carbon content plays, for example, a major role in the analysis of water for contaminations, for example, in wastewater, drinking water, sea water and surface bodies of water, as well as in process water or in water for pharmaceutical applications.

In liquid samples, the carbon contained therein is typically converted to carbon dioxide either wet-chemically or using UV or combustion methods. The sample is combusted in a high-temperature furnace at 670-1200° C. In combustion methods (in particular at temperatures of less than 1000° C.), a catalyst is often used to ensure complete oxidation. In aqueous samples, therefore, in addition to carbon dioxide and other combustion gases, water vapor also arises, and is generally condensed after the combustion and separated from the carbon dioxide gas. Before the carbon dioxide gas is passed into the analysis unit, dusts, aerosols, and other gas constituents are sometimes removed from the carbon dioxide gas using filters and absorbers or adsorbers. A stream of a carrier gas transports the carbon dioxide gas to the analysis unit. Oxygen or mixtures of oxygen with nitrogen or (processed) compressed and ambient air are used as carrier gas, for example. The carbon content is often determined by means of a non-dispersive infrared (NDIR) sensor.

The carrier gas itself should be as free as possible of carbon dioxide so as not to falsify the analysis of the carbon dioxide gas and the determination of the carbon content of the sample. In particular when using a carrier gas containing carbon dioxide (e.g., compressed or ambient air), a binder such as soda lime, also known as caustic soda, is generally used to separate out the carbon dioxide from the carrier gas. The binder must be able to physically and/or chemically bind carbon dioxide gas, for example by means of adsorption or conversion of the carbon dioxide to carbonate.

When soda lime, a mixture of sodium hydroxide and calcium hydroxide, is used, the carbon dioxide gas is reacted with water to give hydronium ions and carbonate; see the following equation:

$$CO_2 + 3H_2O \leftrightarrow 2H_3O^+ + CO_3^{2-}$$

The sodium hydroxide neutralizes the hydronium ions, with formation of water.

$$2H_3O^+ + 2OH^- \leftrightarrow 4H_2O$$

The carbonate is precipitated out by the calcium hydroxide as calcium carbonate.

$$CO_3^{2-} + Ca^{2+} \rightarrow CaCO_3$$

Therefore, the soda lime cannot be used upon falling below a defined water content in the soda lime, since water is essential as a reaction partner in the binding of the carbon dioxide gas. Since the carrier gas can absorb water when the binder is flowing through, there is the risk that the binder will dry out slowly over time.

In order to prevent the soda lime from drying out, it is customary according to the prior art to integrate a vessel with water into the carrier gas stream upstream of the binder. When flowing over or through the water, the carrier gas absorbs water vapor. When the carrier gas impinges on the binder, the binder is moistened by the water vapor contained in the carrier gas and drying out is thereby prevented. Since the water in the vessel is discharged through the carrier gas over time, it must be replaced regularly. This is associated with control and maintenance effort.

SUMMARY

The object of the present disclosure is therefore to provide a TOC analyzer in which the binder can be moistened in a simple manner, and also a corresponding method.

The object is achieved according to the invention by a TOC analyzer for determining a carbon content of a sample, wherein the sample contains at least one analyte and water, comprising:

an inlet for a carrier gas, wherein the carrier gas serves for transporting a carbon dioxide gas resulting from oxidation of the sample to an analysis unit;

a processing unit for removing carbon dioxide gas from the carrier gas before the oxidation of the sample, wherein the processing unit has a binder for binding the carbon dioxide gas from the carrier gas, wherein a defined water content is provided within the binder, wherein the processing unit is provided for moistening the binder by means of water vapor contained in the carrier gas;

a high-temperature furnace for vaporizing and/or oxidizing the sample at a high temperature to form water vapor and carbon dioxide gas;

an injection unit for injecting the sample into the high-temperature furnace;

a condensation unit for condensing the water vapor resulting from the vaporization and/or oxidation of the sample to form a condensate, wherein the condensation unit has an outlet for the condensate toward a moistening unit;

the moistening unit for moistening the carrier gas by means of the condensate; and the analysis unit for determining the carbon content of the sample on the basis of the carbon dioxide gas resulting from the oxidation of the sample.

Typically, between 20 μl and 2000 μl of the aqueous sample is injected into the high-temperature furnace in which the sample is vaporized and/or oxidized. In order to support the oxidation, the carrier gas often comprises oxygen. The resulting water vapor is subsequently condensed in the condensation unit, and the condensate is then provided in the moistening unit. When passing through the moistening unit, the carrier gas absorbs water vapor from the condensate and subsequently delivers it to the binder in the processing unit. The binder is thus moistened by means of the condensate and the carrier gas, and therefore the water content in the binder exceeds a defined threshold value and the binder is functional. When flowing through the moistening unit, the carrier gas can become (nearly) saturated with water vapor, wherein the quantity of the water vapor absorbed by the carrier gas is increased by a large surface area of the condensate. Due to the small sample volume, only a few milliliters of condensate are obtained per hour. However, these few milliliters of water are sufficient to sufficiently increase the water vapor content in the carrier gas so as to prevent the binder from drying out. This makes it possible to ensure the function of the binder, namely binding of carbon dioxide.

A great advantage of the TOC analyzer according to the present disclosure is therefore that the binder is supplied with a defined water content within the TOC analyzer without the need to introduce additional water into the TOC analyzer. Here, a few milliliters of water per hour, which are introduced into the TOC analyzer by the sample(s), are sufficient. In addition, the condensate obtained from the sample has no impurities, or only very few impurities, and is therefore particularly suitable for moistening the binder. Contamination of the binder, in particular the introduction of acids or contact with acidic gas constituents, should absolutely be avoided so as not to impair the function of the binder.

Direct moistening of the binder with condensate without bypassing via the carrier gas is not desirable, since this would lead to structural dissolution of the binder, which in turn would limit the function of the binder, namely the binding of carbon dioxide gas.

The binder preferably has soda lime. Soda lime is a mixture of sodium hydroxide and calcium hydroxide, which can only perform its ability to bind carbon dioxide gas in cooperation with water. Drying out of the soda lime would be accompanied by a significant reduction in the binding ability of the binder.

Advantageously, the carrier gas is ambient air, compressed air, nitrogen or a mixture of gas, in particular a mixture of gas composed of nitrogen and oxygen. The carrier gas must contain at least traces of oxygen in order to enable the oxidation of the sample.

In one possible embodiment, the outlet of the condensation unit is configured as a valve or siphon. The transition between the condensation unit and the moistening unit should be configured such that only the condensate can pass from the condensation unit into the moistening unit and that no carrier gas can enter the condensation unit from the moistening unit. This can be achieved by means of a valve or a siphon.

In a further embodiment, a pump is provided for transporting the condensate from the condensation unit into the moistening unit. The pump facilitates the discharge of the condensate from the condensation unit into the moistening unit and thereby ensures that there is no direct gas connection from the moistening unit to the condensation unit.

A further embodiment provides for the moistening unit to be pipe-like or hose-like so that the carrier gas and the condensate can be guided past one another. For example, the moistening unit is designed such that the condensate runs along an inner wall in at least one region of the moistening unit and the carrier gas flows along the inner wall in the same or the opposite direction. In all embodiments, the moistening unit should always be designed such that the carrier gas can come into contact with the condensate and can thus absorb water vapor.

In an alternative embodiment, the moistening unit has a vessel for collecting the condensate, wherein the carrier gas can be guided through the vessel. Advantageously, the vessel of the moistening unit is provided with a drain so that excess condensate can be discharged from the vessel. Overflow of the vessel should be prevented because otherwise the condensate potentially enters the processing unit and interacts directly with the binder.

The vessel of the moistening unit is preferably configured at least in part as a siphon. Since a lower pressure generally prevails in the condensation unit than in the moistening unit, the siphon makes it possible to ensure that the condensate is discharged into the moistening unit. In an alternative embodiment, the vessel is provided with a fill level sensor which determines and/or monitors the fill level of the condensate within the vessel. The fill level can, for example, be provided to a user on software of the TOC analyzer.

In a further embodiment, a suction device is arranged on the vessel so that, in the event that a predefined fill level of the condensate is exceeded, the condensate can be at least partially suctioned off. As soon as the fill level sensor reports that the fill level exceeds a predetermined threshold value, the suction device is used to prevent overflow of the vessel.

The condensation unit is preferably coolable. The condensation unit may, for example, resemble a cold trap in order to cause the water to pass from the gaseous phase into the liquid phase.

The object is further achieved according to the present disclosure by a method for moistening a binder in a TOC analyzer according to at least one of the preceding claims, wherein the method comprises at least the following steps:
  injecting and vaporizing and/or oxidizing the sample in the high-temperature furnace;
  condensing the water vapor resulting from the vaporization and/or oxidation of the sample in the condensation unit;
  discharging the condensate into the moistening unit;
  moistening the carrier gas by means of the condensate in the moistening unit; and
  moistening the binder by means of the moistened carrier gas in the processing unit.

The method according to the present disclosure advantageously makes it possible to prevent the defined water content of the binder from falling below the defined water content of the binder using a by-product of the TOC analyzer, namely the water vapor produced during the vaporization and/or oxidation of the sample. Providing water for carrier gas moistening in the TOC analyzer can be dispensed with. The amount of water typically contained in the aqueous samples is sufficient for the method according to the invention. In addition, the condensate obtained after the vaporization and/or after the oxidation of the sample is (virtually) completely free of impurities or contaminations and thereby best suited for moistening the binder.

BRIEF DESCRIPTION OF THE DRAWINGS

The present disclosure is explained in more detail below with reference to the following drawings in which.

DETAILED DESCRIPTION

Figure 1:
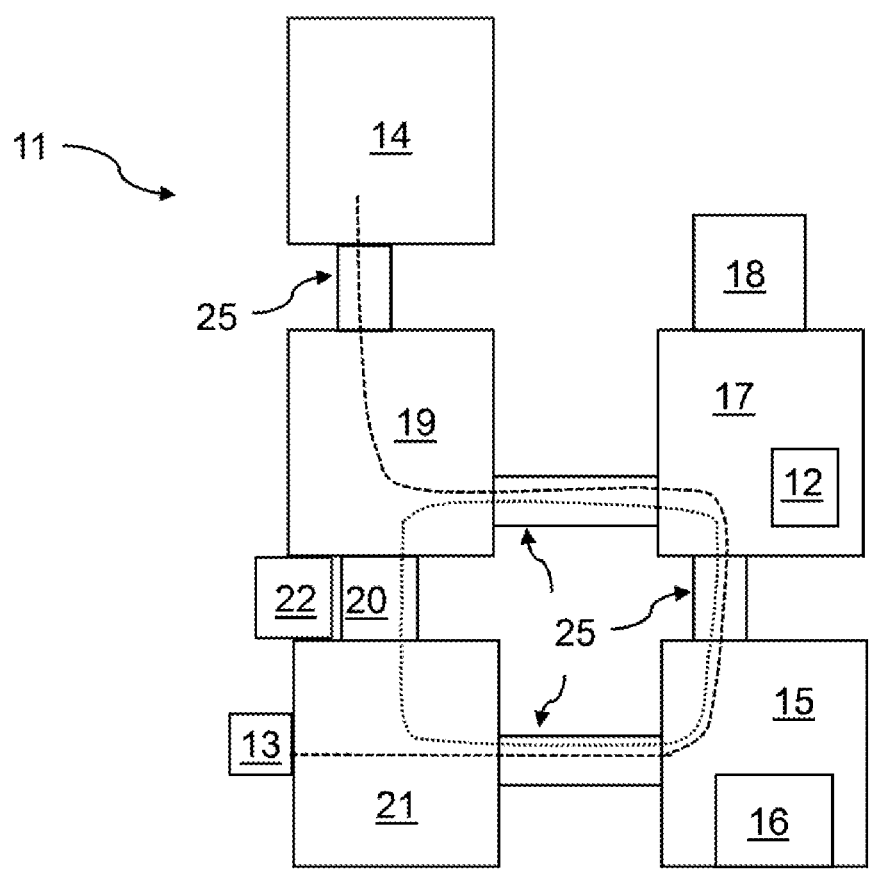
FIG. 1 shows a schematic embodiment of the TOC analyzer according to the present disclosure.

The TOC analyzer 11 according to the present disclosure is schematically illustrated in FIG. 1. The TOC analyzer 11 serves to determine a carbon content of a sample 12, which is present in water. The sample 12 is introduced, for example, injected, into a high-temperature furnace 17 by means of an injection unit 18. The high-temperature furnace 17 is at its reaction temperature of between 670-1200° C. such that vaporization and/or oxidation of the sample 12 occurs. The resulting water vapor is condensed in a condensation unit 19, for example, by a coolable condensation unit. The carbon dioxide gas resulting from the vaporization and/or oxidation of the sample 12 is transported using a carrier gas to the analysis unit 14, in which the carbon content is determined. The carrier gas can be, for example, ambient air, compressed air, nitrogen or a mixture of gas, in particular a mixture of gas composed of nitrogen and oxygen. If the carrier gas has at least traces of carbon dioxide gas, such gas must be removed from the carrier gas before it is introduced into the high-temperature furnace 17. The carrier gas is introduced into the TOC analyzer via an inlet 13. This generally takes place by means of a compressor or by means of compressed air. The carrier gas is typically guided through the TOC analyzer from the inlet 13 to the analysis unit 14 by means of a suitable pressure. The path of the carrier gas is represented by dashed lines in FIG. 1. The dotted lines approximately represent between which units the water or the water vapor moves.

A binder 16, e.g., soda lime, is provided in the processing unit 15, which binder extracts the carbon dioxide gas from the carrier gas and binds it. In order for the binder 16 to be able to fulfill its function, a defined water content of the binder 16 must not be undershot. Since the carrier gas can absorb water from the binder 16 when it flows through the processing unit 15, there is the risk that the binder 16 will slowly dry out over time. For this reason, condensate 26 formed in the condensation unit 19 is collected and discharged via an outlet 20 to a moistening unit 21. The outlet 20 can be configured, for example, as a valve or a siphon in order to prevent the transfer of carrier gas from the moistening unit 21 into the condensation unit 19. Optionally, a pump 22 may also be used to pump the condensate 26 out of the condensation unit 19 and into the moistening unit 21.

The condensate 26 is provided in the moistening unit 21 and brought into contact with the carrier gas so that the carrier gas is moistened by the condensate 26. When the carrier gas subsequently flows into the processing unit 15, the water vapor absorbed by the carrier gas in the moistening unit 21 can moisten the binder 16. The moistening of the binder 16 is thus ensured by an internal process of the TOC analyzer 11. The connecting members 25 between the various units, for example, the connection between the moistening unit 21 and the processing unit 15, are shown in FIG. 1 by way of example as pipes. There is no limitation on the connections and transitions between the individual units and the exact arrangement thereof.

Figure 2A:
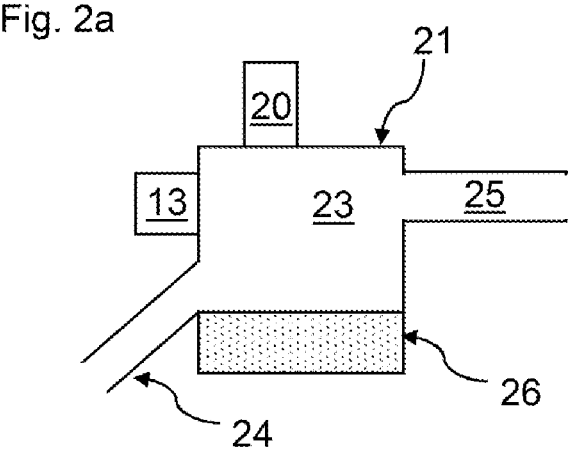
FIG. 2a shows a first embodiment according to the present disclosure of a moistening unit.
Figure 2B:
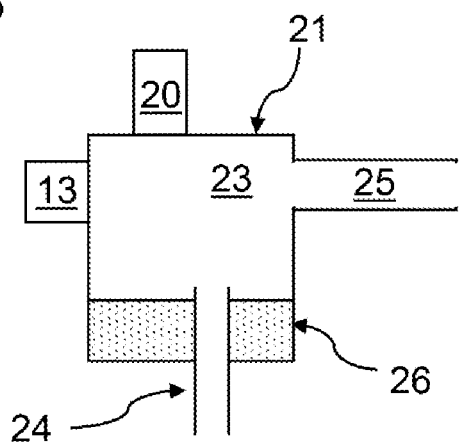
FIG. 2b shows a second embodiment according to the present disclosure of the moistening unit.
Figure 2C:
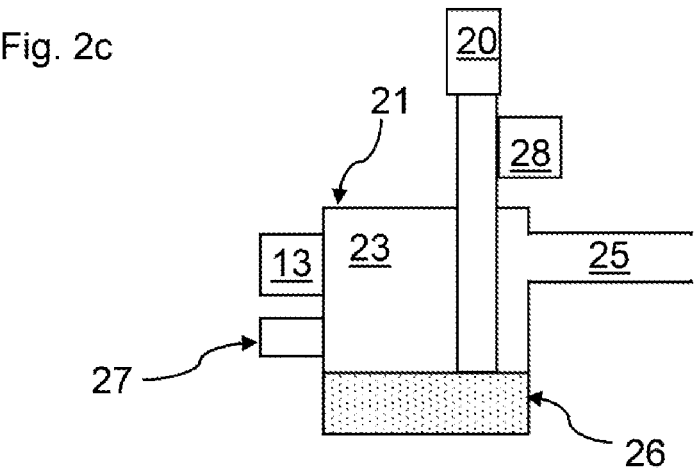
FIG. 2c shows a third embodiment according to the present disclosure of the moistening unit.
Figure 2D:
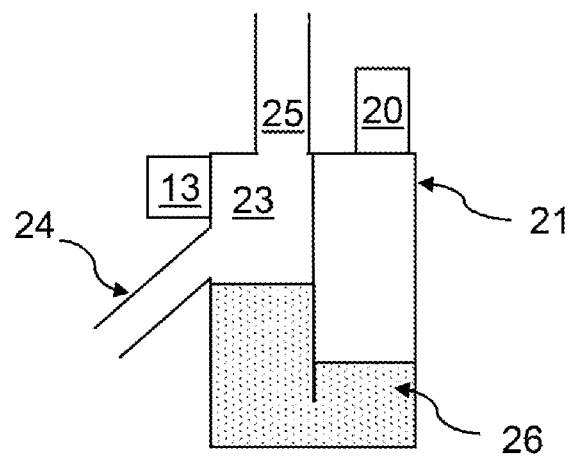
FIG. 2d shows a fourth embodiment according to the present disclosure of the moistening unit.

FIGS. 2a-2d show four different embodiments of the moistening unit 21, wherein the moistening unit 21, for example, in each case has a vessel 23 for collecting the condensate 26 and the carrier gas flows in each case through the vessel 23. FIG. 2a shows the vessel 23 provided with a drain 24 on a wall of the vessel 23 so that an excess of condensate 26 can be discharged from the vessel 23. Alternatively, as shown in FIG. 2b, the drain 24 may also be mounted in the center of the vessel 23. In order to prevent overflow of the vessel 23, a fill level sensor 27 can alternatively also be attached to the vessel 23, which sensor serves to determine and/or monitor the fill level of the condensate 26 in the vessel 23. If the fill level exceeds a predefined fill level, the condensate 26 can be at least partially suctioned off from the vessel 23 by means of a suction device 28 so that the fill level in the vessel 23 falls back below the predefined fill level. In addition to the vessel 23, the moistening unit 21 can also have an integrated siphon, as schematically shown in FIG. 2d.

Figure 3A:
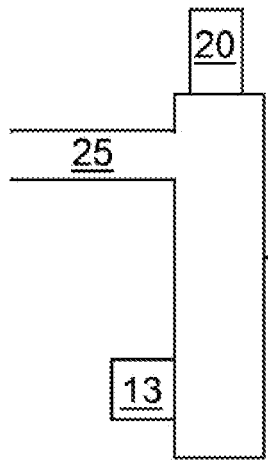
FIG. 3a shows a fifth embodiment according to the present disclosure of the moistening unit.
Figure 3B:
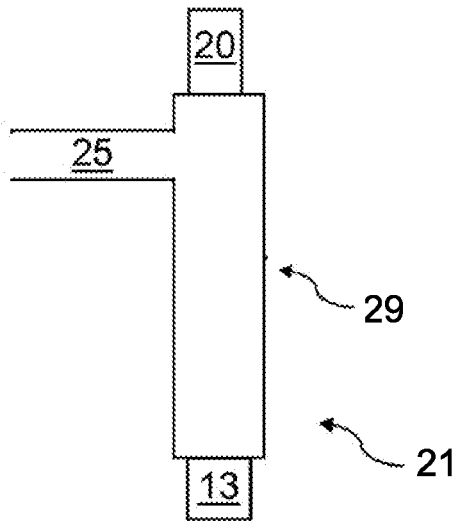
FIG. 3b shows a sixth embodiment according to the present disclosure of the moistening unit.

In FIGS. 2a-2d, analogously to FIG. 1, the inlet 13 for the carrier gas and the outlet 20 for the condensate are attached by way of example to the vessel 23 or the moistening unit 21. The exact arrangement of the individual units is not limited to this embodiment, but can also take place in another way familiar to those skilled in the art. This also applies to FIGS. 3a and 3b. FIGS. 3a and 3b show two further alternative embodiments of the moistening unit 21. Instead of a vessel 23, the moistening unit 21 has a pipe-like or hose-like arrangement. The condensate 26 (not shown) is introduced via the outlet 20 into the pipe 29 and, for example, runs along an inner wall of the pipe 29. The carrier gas flows through the pipe 29 and absorbs water vapor through contact with the moist surface.

Figure 4:
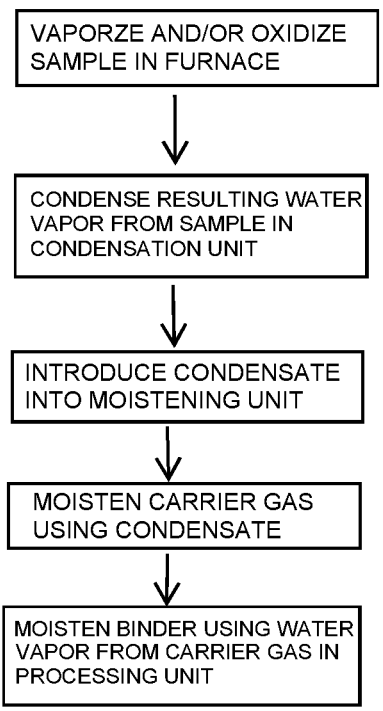
FIG. 4 shows a flowchart of an exemplary embodiment of a method according to the present disclosure.

FIG. 4 shows an exemplary embodiment of the method according to the present disclosure, which can be implemented using a TOC analyzer 11 from the previous figures and which serves to moisten a binder 16 in a TOC analyzer 11. In a first step 1 of the method, the sample 12 is injected into the high-temperature furnace 17 and vaporized and/or oxidized. Subsequently, in a second step 2, the water vapor resulting from the vaporization and/or oxidation of the sample 12 is condensed in the condensation unit 19 so that a condensate 26 is formed. In a third step 3, this condensate 26 is introduced into the moistening unit 21, in which, in the fourth step 4, the carrier gas is moistened by means of the condensate 26. In the fifth step 5, the binder 16 is finally moistened in the processing unit 15 by means of the water vapor contained (e.g., entrained) in the carrier gas.

We claim:

1. A TOC analyzer for determining a carbon content of a sample, wherein the sample contains at least one analyte and water, the analyzer comprising:

an inlet adapted to convey a carrier gas, wherein the carrier gas is provided as to transport a carbon dioxide gas resulting from oxidation of the sample to an analysis unit;

a processing unit configured to remove carbon dioxide gas from the carrier gas before the oxidation of the sample, wherein the processing unit includes a binder selected for binding the carbon dioxide gas from the carrier gas, wherein a defined water content is provided within the binder, wherein the processing unit is further configured to moisten the binder using water vapor contained in the carrier gas;

a high-temperature furnace configured to vaporize and/or oxidize the sample at a high temperature to form water vapor and carbon dioxide gas;

an injection unit adapted to inject the sample into the high-temperature furnace;

a condensation unit configured to condense the water vapor resulting from the vaporization and/or oxidation of the sample to form a condensate, wherein the condensation unit includes an outlet for the condensate and is connected to a moistening unit;

the moistening unit, which is adapted to moistening the carrier gas using the condensate; and the analysis unit, which is configured to determine the carbon content of the sample based on the carbon dioxide gas resulting from the oxidation of the sample.

2. The analyzer of claim 1, wherein the binder comprises soda lime.

3. The analyzer of claim 1, wherein the carrier gas is ambient air, compressed air, nitrogen, or a mixture of gas comprising nitrogen and oxygen.

4. The analyzer of claim 1, wherein the outlet of the condensation unit is configured as a valve or siphon.

5. The analyzer of claim 1, further comprising a pump configured to facilitate transporting the condensate from the condensation unit into the moistening unit.

6. The analyzer of claim 1, wherein the moistening unit is pipe-like or hose-like such that the carrier gas and the condensate can be guided past one another.

7. The analyzer of claim 1, wherein the moistening unit includes a vessel configured to collect the condensate and to enable the carrier gas to be guided through the vessel.

8. The analyzer of claim 7, wherein the vessel of the moistening unit includes a drain configured such that excess condensate can be discharged from the vessel.

9. The analyzer of claim 7, wherein the vessel is configured at least in part as a siphon.

10. The analyzer of claim 7, wherein the vessel includes a fill level sensor configured to determine and/or monitor the fill level of the condensate within the vessel.

11. The analyzer of claim 10, the moistening unit includes a suction device arranged on the vessel such that, when a predefined fill level of the condensate is exceeded, the condensate is at least partially suctioned out of the vessel.

12. The analyzer of claim 1, wherein the condensation unit is adapted to be cooled.

13. A method for moistening a binder in a TOC analyzer, the method comprising:

injecting and vaporizing and/or oxidizing a sample in the high-temperature furnace;

condensing water vapor resulting from the vaporization and/or oxidation of the sample in a condensation unit as a condensate;

discharging the condensate into the moistening unit;

moistening the carrier gas using the condensate in the moistening unit; and moistening the binder using the moistened carrier gas in a processing unit configured to remove carbon dioxide gas from the carrier gas before the oxidation of the sample, wherein the processing unit includes the binder, which is selected for binding the carbon dioxide gas from the carrier gas, wherein the processing unit is further configured to moisten the binder using water vapor contained in the carrier gas to a defined water content.

* * * * *